United States Patent
Kloog et al.

(10) Patent No.: US 8,268,889 B2
(45) Date of Patent: Sep. 18, 2012

(54) TREATMENT OF OVARIAN CANCER

(75) Inventors: Yoel Kloog, Herzliya (IL); Gilad Ben-Baruch, Tel Aviv (IL)

(73) Assignee: Ramot at Tel-Aviv University Ltd. (IL)

( * ) Notice: Subject to any disclaimer, the term of this patent is extended or adjusted under 35 U.S.C. 154(b) by 585 days.

(21) Appl. No.: 12/223,676

(22) PCT Filed: Feb. 1, 2007

(86) PCT No.: PCT/IL2007/000129
§ 371 (c)(1),
(2), (4) Date: Jan. 7, 2009

(87) PCT Pub. No.: WO2007/091241
PCT Pub. Date: Aug. 16, 2007

(65) Prior Publication Data
US 2009/0226539 A1    Sep. 10, 2009

Related U.S. Application Data

(60) Provisional application No. 60/772,324, filed on Feb. 10, 2006.

(51) Int. Cl.
*A61K 31/20* (2006.01)
*A61K 31/10* (2006.01)
(52) U.S. Cl. .................. 514/568; 514/712
(58) Field of Classification Search ........... 514/568, 514/712
See application file for complete search history.

(56) References Cited

U.S. PATENT DOCUMENTS
5,705,528 A * 1/1998 Kloog .................... 514/524

FOREIGN PATENT DOCUMENTS
WO  WO-95/13059 A1    5/1995
WO  WO-2005/018562 A2    3/2005
WO  WO-2006/023639 A1    3/2006

OTHER PUBLICATIONS

Chabner BA, Ryan DP, Paz-Ares L, Garcia-Carbonero R, and Calabresi P, "Chapter 52—Antineoplastic agents" Goodman & Gilman's The Pharmacological Basis of Therapeutics 10th ed., Hardman JG, Limbird LE, and Gilman AG, Eds, McGraw-Hill, New York 2001, 1389-1460 (pp. 1389, and 1432-1434 provided).*
Dinulescu DM, Ince TA, Quade BJ, Shafer SA, Crowley D, Jacks T. Role of K-ras and Pten in the development of mouse models of endometriosis and endometrioid ovarian cancer. Nat Med. Jan. 2005;11(1):63-70.*
Wilkinson GR, Chapter 1 Pharmacokinetics—The Dynamics of Drug Absorption, Distribution, and Elimination, "Goodman & Gilman's The Pharmacological Basis of Therapeutics, 10th ed." Hardman JG, Limbird LE, and Gilman AG, Eds., McGraw-Hill, 2001, 3-30.*
Anderson PL, King T, Zheng JH, and MaWhinney S, "Cytokine and sex hormone effects on zidovudine- and lamivudine-triphosphate concentrations in vitro," Journal of Antimicrobial Chemotherapy, Oct. 2008, 62(4), 738-745.*
Gura T, "Systems for Identifying New Drugs Are Often Faulty," Science Nov. 1997, 278(5340), 1041-1042.*
Zhao L, Wientjes MG, Au JL. Evaluation of combination chemotherapy: integration of nonlinear regression, curve shift, isobologram, and combination index analyses. Clin Cancer Res. Dec. 1, 2004;10(23):7994-8004.*
Biener et al., "Ras antagonist inhibits growth and chemosensitizes human epithelial ovarian cancer cells", International Journal of Gynecological Cancer, vol. 16, Suppl. 1, pp. 200-206, Jan. 2006.
Marom et al., "Selective Inhibition of Ras-dependent Cell Growth by Farnesylthiosalisylic Acid", Journal of Biological Chemistry, American Society of Biochemical Biologists, vol. 270, No. 38, pp. 22263-22270, Sep. 22, 1995, Birmingham, US.
Gana-Weisz et al, "The Ras inhibitor S-trans,*trans*-Farnesylthiosalicylic Acid Chemosensitizes Human Tumor Cells Without Causing Resistance", Clinical Cancer Research, vol. 8, No. 2, pp. 555-565, Feb. 2002.

* cited by examiner

*Primary Examiner* — Paul Zarek
(74) *Attorney, Agent, or Firm* — Lerner, David, Littenberg, Krumholz & Mentlik, LLP

(57) ABSTRACT

Disclosed are methods of treating ovarian cancer by administering an effective amount of FTS (farnesylthiosalicylic acid), or various analogs thereof, or a pharmaceutically acceptable salt, optionally with, a platinum-based chemotherapy drug to a human diagnosed with ovarian cancer.

10 Claims, 4 Drawing Sheets

TREATMENT OF OVARIAN CANCER

CROSS REFERENCE TO RELATED APPLICATIONS

The present application is a national phase entry under 35 U.S.C. §371 of International Application No. PCT/IL2007/000129, filed Feb. 1, 2007, published in English, which claims benefit of U.S. Provisional Patent Application No. 60/772,324 filed Feb. 10, 2006. The disclosures of all of said applications are incorporated by reference herein.

BACKGROUND OF THE INVENTION

Ovarian cancer represents a major clinical challenge in gynecologic oncology. Most patients are asymptomatic until the disease has metastasized, two-thirds are diagnosed only at an advanced stage. As a result, ovarian cancer has the highest fatality-to-case ratio of all gynecologic malignancies. In spite of cytoreductive surgery and combination chemotherapy, the 5-year survival rate of patients with advanced ovarian cancer is only 20-30%. [Holschneider, C. H. and Berek J. S., Semin. Surg. Oncol. 19:3-10 (2000)].

Ovarian cancer develops mainly from the malignant transformation of a single cell type, the surface epithelium. Although the biologic mechanism of transformation remains unclear, it is reported to involve a multi-step process requiring an accumulation of genetic lesions that affect several different classes of genes. [Holschneider, supra.].

Oncogenes encode proteins that participate in growth-stimulatory pathways in normal cells. Activation of these genes (as a result of amplification, translocation, or mutation) contributes to the development of epithelial ovarian cancers. [Holschneider, supra.].

One method of treating these epithelial ovarian cancers entails administration with platinum-based chemotherapy drugs or platinates. Platinates are cytotoxic drugs containing a core atom of platinum, including cisplatin, carboplatin and analogs thereof. They are DNA-damaging agents and are used in the treatment of cancer because of their efficacy. Cisplatin (cis-diamminedichloroplatinum) is used particularly in the treatment of solid tumors. It has been reported that aggressive regimens of cisplatin and its analog carboplatin boost the clinical response rates of advanced ovarian cancer to 60-80%, but 30-40% of initial responders subsequently relapse with tumors that resist cisplatin. [Holschneider, supra.]. Thus, the toxicity of these agents and the development of resistance to these agents continues to be problematic.

SUMMARY OF THE INVENTION

A first aspect of the present invention is directed to a method of treating ovarian cancer. The method comprises administering to a patient (human) in need thereof an effective amount of farnesylthiosalicylic acid (FTS) or an analog thereof, or a pharmaceutically acceptable salt thereof.

Another aspect of the present invention is directed to a method of treating ovarian cancer which comprises administering to a patient (human) in need thereof an effective amount of farnesylthiosalicylic acid (FTS) or an analog thereof or a pharmaceutically acceptable salt thereof, and a platinum-based drug (e.g., cisplatin or an analog thereof).

Another aspect of the present invention is directed to a method of inhibiting growth of human ovarian cancer cells which comprises contacting human ovarian cancer cells with an effective amount of farnesylthiosalicylic acid (FTS) or an analog thereof or a pharmaceutically acceptable salt thereof.

Another aspect of the present invention is directed to a method of inhibiting growth of human ovarian cancer cells which comprises contacting human ovarian cancer cells with an effective amount of farnesylthiosalicylic acid (FTS) or an analog thereof or a pharmaceutically acceptable salt thereof, and a platinum-based drug (e.g., cisplatin or an analog thereof).

Another aspect of the present invention is directed to a method of chemosensitizing human ovarian cancer cells which comprises contacting human ovarian cancer cells with an effective amount of farnesylthiosalicylic acid (FTS) or an analog thereof or a pharmaceutically acceptable salt thereof, and then contacting the cells with an effective amount of a platinum-based drug (e.g., cisplatin) or an analog thereof.

The results of experiments described herein demonstrate that in a common ovarian cancer cell line used in the study of ovarian cancer, and which is resistant to cisplatin, FTS promoted apoptosis of malignant cells and increased sensitivity to cisplatin. Thus, the effect was greater than additive. Thus, combined treatment with FTS allows use of relatively low dosages of the platinum-based drug, which is associated lower toxicity and fewer side effects.

DETAILED DESCRIPTION

Figure 1A:
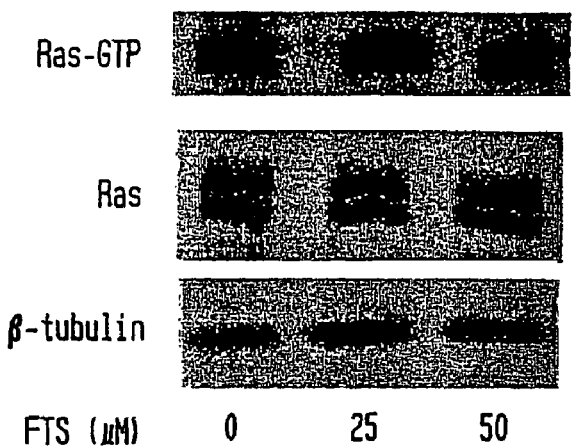
FIG. 1A depicts images of Western immunoblot assays displaying levels of Ras-GTP and Ras, and β-tubulin in OVCAR-3 cells treated with 0 μM, 25 μM, and 50 μM FTS.

Ras proteins act as on-off switches that regulate signal-transduction pathways controlling cell growth, differentiation, and survival. [Reuther, G. W., Der, C. J., Curr Opin Cell Biol 12:157-65 (2000)]. They are anchored to the inner leaflet of the plasma membrane, where activation of cell-surface receptors, such as receptor tyrosine kinase, induces the exchange of guanosine diphosphate (GDP) for guanosine triphosphate (GTP) on Ras and the conversion of inactive Ras-GDP to active Ras-GTP. [Scheffzek, K., Ahmadian, M. R., Kabsch, W. et al. Science 277:333-7 (1997)]. The active Ras protein promotes oncogenesis through activation of multiple Ras effectors that contribute to deregulated cell growth, differentiation, and increased survival, migration and invasion. See e.g., Downward, J., Nat. Rev. Cancer 3:11-22 (2003); Shields, J. M., et al., Trends Cell Biol 10:147-541 (2000); and Mitin, N., et al., Curr Biol 15:R563-74 (2005). U.S. Pat. No. 5,705,528 discloses farnesylthiosalicylic acid (FTS) and analogs thereof and their utility as anti-cancer agents. FTS is believed to exert its antagonistic effect by dislodging activated Ras from its membrane anchor protein, thus deactivating activated Ras. See, Haklai, et al., Biochemistry 37(5):1306-14 (1998).

FTS and its analogs are represented by formula I:

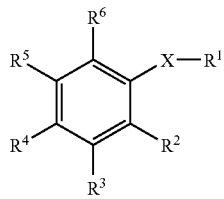

wherein $R^1$ represents farnesyl, geranyl or geranyl-geranyl;

$R^2$ is $COOR^7$, or $CONR^7R^8$, wherein $R^7$ and $R^8$ are each independently hydrogen, alkyl or alkenyl;

$R^3$, $R^4$, $R^5$ and $R^6$ are each independently hydrogen, alkyl, alkenyl, alkoxy, halo, trifluoromethyl, trifluoromethoxy, or alkylmercapto; and X represents S.

The structure of FTS is as follows:

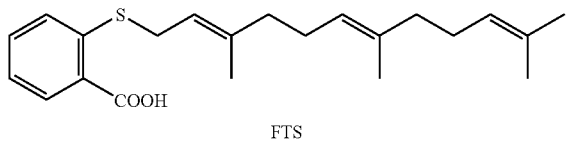

FTS

FTS analogs embraced by formula I include 5-fluoro-FTS, 5-chloro-FTS, 4-chloro-FTS, S-farnesyl-thiosalicylic acid methyl ester (FTSME), and S-geranyl,geranyl-thiosalicylic acid (GGTS). Structures of these compounds are set forth below.

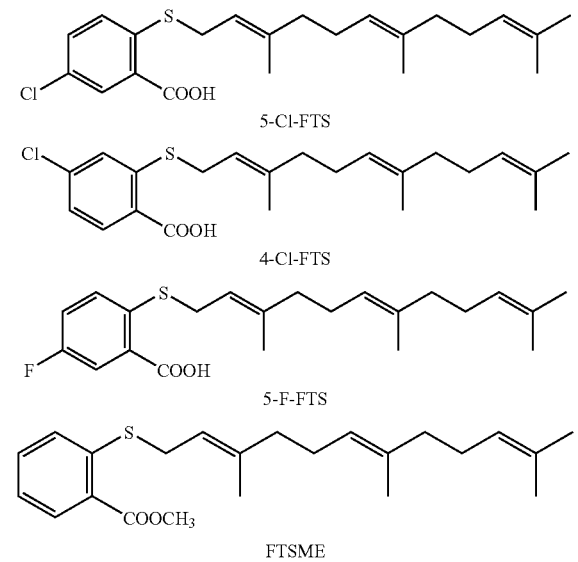

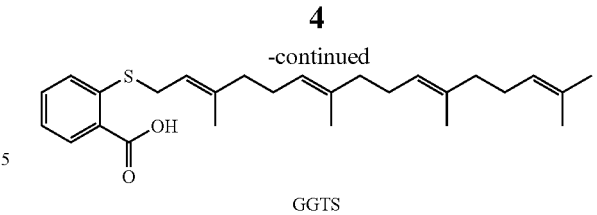

GGTS

Methods for preparing the compounds of formula I are disclosed in U.S. Pat. Nos. 5,705,528 and 6,462,086. See also, Marom, M., Haklai, R., Ben-Baruch, G., Marciano, D., Egozi, Y., Kloog, Y. J Biol Chem 270:22263-70 (1995).

Pharmaceutically acceptable salts of the Ras antagonists of formula I may be useful. These salts include, for example, sodium and potassium salts. Other pharmaceutically acceptable salts may be selected in accordance with standard techniques as described in Berge, S. M., Bighley, L. D., and Monkhouse, D. C., J. of Pharm. Sci. 66(1):1-19 (1977). In preferred embodiments, however, the Ras antagonist, e.g., FTS and its analogs, are not in the form of a salt (i.e., non-salified).

The platinum-based drugs useful in the practice of the present invention include cisplatin [cis-diamminedichloroplatinum(II)] and its analogs, e.g., carboplatin [diammine(1,1-cyclobutanedicarboxylato)platinum(II)]. These drugs are known to inflict damage on cellular nucleic acids, including DNA. Cisplatin acts by cross-linking DNA in various different ways, making it impossible for rapidly dividing cells to duplicate their DNA for mitosis. The damaged DNA sets off DNA repair mechanisms, which activate apoptosis when repair proves impossible.

Methods of preparing and using cisplatin as an anti-cancer agent are described in, for example, U.S. Pat. No. 5,562,925.

Carboplatin differs from cisplatin in that it has a closed cyclobutane dicarboxylate moiety on its leaving group in contrast to the readily leaving chloro groups. This results in very different DNA binding kinetics.

Methods of preparing and using carboplatin as an anti-cancer agent are described in, for example, U.S. Pat. No. 4,657,927.

The cancers treatable in accordance with the present invention comprise epithelial ovarian cancers. Surface epithelial tumors account for approximately 60% of all ovarian neoplasms and 80-90% of malignant ovarian tumors. Serous tumors are the most common subtype and the most common type of malignant ovarian tumor in adults. Surface epithelial neoplasms are also classified into subtypes based on the type of epithelial differentiation that is present in the tumor. The subtypes include serous, mucinous, endometrioid, clear cell, and transitional cell. The subtypes derive their names from the tissue that they most closely resemble. For example, subtype serous most closely resembles fallopian tube epithelium; subtype mucinous most closely resembles GI tract or endocervical epithelium; subtype endometrioid most closely resembles proliferative endometrium; subtype clear cell most closely resembles gestational endometrium; and subtype transitional cell (Brenner) most closely resembles urinary tract epithelium.

The frequency of administration, dosage amounts, and the duration of treatment of each of the active agents may be determined depending on several factors which may include the overall health, size and weight of the patient, the severity and type of the ovarian cancer, the patient's tolerance to the treatment, and the particular treatment regimen being administered. For example, duration of treatment with FTS or the combination of FTS and the other active may last a day, a week, a year, or until remission of the cancer is achieved. Thus, relative timing of administration of each active agent is not critical (e.g., FTS may be administered before, during, and after treatment with the platinum-based drug).

As used herein, the term "effective amount" refers to the dosages of FTS alone or in combination with the other active that are effective for the treating, and thus includes dosages that ameliorate symptom(s) of the cancer, diminish extent of disease, delay or slow or prevent disease progression, or achieve partial or complete remission or prolong survival. The average daily dose of FTS generally ranges from about 50 mg to about 1000 mg, and in some embodiments, ranges from about 200 mg to about 600 mg. The average daily dose of cisplatin generally ranges from about –10 mg to about 170 mg, and in some embodiments about 10 mg to about 120 mg. The average daily dose for carboplatin generally ranges from about 30 mg to about 620 mg, and in some embodiments about 30 mg to about 400 mg.

In some embodiments, both drugs are administered on a daily basis, e.g., each in single once-a-day or divided doses. They may be administered at the same or different times. In other embodiments, each drug is administered two or more times per day.

The methods of the present invention may be used for the treatment of cancer in mammals, particularly humans. The actives may be administered in accordance with standard methods. In preferred embodiments, FTS is administered orally. Accordingly, FTS may be administered by dosing orally daily for three weeks with a one-week "off period" and repeating until remission is achieved. In an oral dosage form, the FTS is typically present in a range of about 100 mg to about 500 mg, and in some embodiments, FTS ranges from about 100 mg to about 300 mg.

In preferred embodiments, the platinum-based drug, e.g., cisplatin, is administered intravenously. Cisplatin and carboplatin are typically administered as a drip infusion into the vein through a cannula. They may also be given through a central line, which is inserted under the skin into a vein near the collarbone, or into a PICC line which is inserted into a vein in the crook of the arm.

In an embodiment, cisplatin is administered in a single intravenous dose every three to four weeks. Under this regimen, the cisplatin is typically administered in an amount of about 50 mg to about 170 mg, and in some embodiments, ranges from about 50 mg to about 120 mg. In another embodiment, cisplatin is intravenously administered on a daily basis for five-days with a three to four-week interval or "off period" before repeating administration. Under this regimen, cisplatin is typically administered in an amount of about 10 mg to about 35 mg, and in some embodiments, ranges from about 10 mg to about 25 mg In an embodiment, carboplatin is administered in a single intravenous dose every three to four weeks. Under this regimen, the carboplatin is typically administered in an amount of about 100 mg to about 600 mg, and in some embodiments, ranges from about 100 mg to about 400 mg. In another embodiment, carboplatin is intravenously administered on a daily basis for five-days with a three to four-week interval or "off period" before repeating administration. Under this regimen, the carboplatin is typically administered in an amount of about 30 mg to about 150 mg, and in some embodiments ranges from about 30 mg to about 75 mg.

Administration of FTS and the platinum-based drug, (e.g., cisplatin) may be cyclic and repeated until remission is achieved. For example, in one treatment regimen, the Ras antagonist and platinum-based drug are administered according to the following schedule: (1) administering FTS and cisplatin daily for a period of five-days followed by a four-week interval without actives ("off period"); and (2) repeating step (1) as many times as needed, e.g., until remission is achieved. Under this regimen, actives are administered in one-week cycles each separated by a four-week off period. In another embodiment, step (1) further includes oral dosing with FTS for an additional three weeks followed by a one-week "off period" before repeating step (1).

Oral compositions for FTS and its analogs for use in the present invention can be prepared by mixing the active with a pharmaceutically acceptable carrier. Suitable carriers are generally solid or liquid. Compositions suitable for oral administration that contain the active are preferably in solid dosage forms such as tablets (e.g., including film-coated, sugar-coated, controlled or sustained release); capsules, e.g., hard gelatin capsules (including controlled or sustained release) and soft gelatin capsules, and powders or granules. The compositions, however, may be contained in other carriers that enable administration to a patient in other oral forms, e.g., a liquid or gel. In any such form, the composition is divided into individual or combined doses containing predetermined quantities of the active ingredients.

Oral dosage forms may be prepared by mixing the active pharmaceutical ingredient or ingredients with one or more appropriate carriers (excipients), and then formulating the composition into the desired dosage form e.g., compressing the composition into a tablet or filling the composition into a capsule or a pouch. Typical excipients useful as bulking agents or diluents, binders, buffers or pH adjusting agents, disintegrants (including crosslinked and super disintegrants such as croscarmellose), glidants, and/or lubricants include lactose, starch, mannitol, microcrystalline cellulose, ethyl cellulose, sodium carboxymethyl cellulose, hydroxypropylmethyl cellulose, dibasic calcium phosphate, acacia, gelatin, stearic acid, magnesium stearate, corn oil, vegetable oils, and polyethylene glycols, and others known to the pharmaceutical practitioner. Coating agents such as sugar, shellac, and synthetic polymers may be employed. Dyes and other colorants and preservatives may be added as well. See, *Remington's Pharmaceutical Sciences*, The Science and Practice of Pharmacy, 20th Edition, (2000).

Liquid form compositions include, for example, solutions, suspensions, emulsions, syrups, elixirs and pressurized compositions. The active ingredient or ingredients, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmoregulators.

Suitable examples of liquid carriers for oral administration include water (particularly containing additives as above, e.g., cellulose derivatives, preferably in suspension in sodium carboxymethyl cellulose solution), alcohols (including monohydric alcohols (including monohydric alcohols and polyhydric alcohols, e.g., glycerin and non-toxic glycols) and their derivatives, and oils (e.g., fractionated coconut oil and arachis oil).

Carriers suitable for preparation of compositions for parenteral administration include Sterile Water for Injection, Bacteriostatic Water for Injection, Sodium Chloride Injection (0.45%, 0.9%), Dextrose Injection (2.5%, 5%, 10%), Lactated Ringer's Injection, and the like. Dispersions can also be prepared in glycerol, liquid polyethylene glycols and mixtures thereof, and in oils. Compositions may also contain tonicity agents (e.g., sodium chloride and mannitol), antioxidants (e.g., sodium bisulfite, sodium metabisulfite and ascorbic acid) and preservatives (e.g., benzyl alcohol, methyl paraben, propyl paraben and combinations of methyl and propyl parabens).

The compositions provided herein may be packaged as kits which comprises printed materials including instructions for treating a human diagnosed with ovarian cancer and an effective amount of farnesylthiosalicylic acid (FTS) or an analog thereof or a pharmaceutically acceptable salt thereof and, optionally, an effective amount of a platinum-based drug (e.g., cisplatin) or an analog thereof. Examples of packaging materials for use in packaging compositions of the present invention include, for example, blister packs, bottles, tubes, pumps, bags, vials, containers, syringes, and any packaging material suitable for a selected formulation and intended mode of administration and treatment.

The efficacy of the methods and compositions of the invention are demonstrated in various in vitro studies confirming the enhanced effects of farnesylthiosalicylic acid (FTS), alone, and in combination with cisplatin on human ovarian carcinoma cells (OVCAR-3).

EXPERIMENTAL DESIGN

The purpose of the following experiments was to determine whether FTS alone inhibited growth of human ovarian cells, and whether FTS chemosensitized these cells to cisplatin, thus providing an effective combination therapy for ovarian cancer. The experiments were performed in vitro using the OVCAR-3 cell line, which is a common cell line used in the treatment of ovarian cancer. The cell line was derived from a patient who was refractory to cisplatin treatment. As a result, the OVCAR-3 cells are cisplatin-resistant. The results indicated that significant amounts of Ras and Ras-GTP were expressed by OVCAR-3 cells and were reduced by 40% using FTS alone. FTS inhibited OVCAR-3 cell growth in a dose-dependent manner. Additionally, when combined with cisplatin, FTS reduced the number of OVCAR-3 cells by 80%, demonstrating a enhanced effect with the combination therapy. Moreover, FTS at a concentration range that allows downregulation of Ras and Ras-GTP in OVCAR-3 cells, also chemosensitizes these cells and can lead to enhanced tumor cell growth inhibition or death.

Materials and Methods

FTS was provided by Concordia Pharmaceuticals, Inc. The purity of the compounds, as assessed by thin-layer chromatography, H1-nuclear magnetic resonance, and mass spectral analysis, was greater than 95%. Compounds for each set of experiments were prepared in chloroform (0.1 M stock solutions) and kept at −70° C. The chloroform was removed from the stock solution by a stream of nitrogen prior to use, and FTS was then dissolved in dimethyl sulfoxide (DMSO). The FTS/DMSO solution was diluted with Roswell Park Memorial Institute 1640 medium containing 10% fetal calf serum (Biological Industries, Beit Ha-Emek, Israel) to yield a ×100 drug-stock solution containing 10% DMSO.

Cell Culture Procedures

The human epithelial ovarian cell line OVCAR-3 was obtained from the American Tissue Culture Collection. Cells were routinely grown in Roswell Park Memorial Institute 1640 medium containing 10% fetal calf serum, 0.1 mM non-essential amino acids, and 2 mM L-glutamine, at 37° C. in a humidified atmosphere of 95% air/5% $CO_2$. To examine the effect of FTS on the anchorage-dependent cell growth, cells were plated at a density of $10 \times 10^4$ cells per well in 24-well plates to which either 0.1% DMSO (control) or the test concentrations of FTS were added after 24 h. Treated cells were grown for 6 or 9 days. Cells were stained with 3-(4,5-dimethylthiosol-2-yl)-2,5-diphenyltetrazolium bromide (MTT, Sigma Chemical Co., St. Louis, Mo.), incubated for 90 min, and dissolved in 0.3 mL of 100% DMSO. The extent of staining was determined spectrophotometrically ($A_{570}$, $A_{630}$) using an enzyme-linked immunosorbent assay reader. All assays were carried out in quadruplicate samples and were repeated three times.

Cytotoxicity Assays

Cisplatin (Sigma) was prepared as a 1 mg/mL stock solution in phosphate-buffered saline. Cells were plated at a density of $10 \times 10^4$ cells per well in 24-well plates. For determination of the median lethal dose, increasing concentrations of cisplatin were added to the cells after 24 h, and plates were incubated for 4 h at 37° C. Cisplatin concentrations ranged from 0.25 to 20 µg/mL. The supernatant was aspirated, and the cells were resupplied with complete medium. The assay was terminated after 72 h. Cells were stained and evaluated with MTT as described previously. All cytotoxicity assays were performed three times in quadruplicate samples.

Chemosensitization

OVCAR-3 cells were plated at a density of $10 \times 10^4$ cells per well in 24-well plates and grown for 3 days in the presence of 50 µM FTS. Cisplatin was then added for 4 h. This protocol was chosen in order to induce only a small cytotoxic effect, thus enabling a determination of any possible enhanced effect with the Ras inhibitor. The number of live cells was evaluated 3 days later by MTT, as described earlier.

Determination of Ras, Ras-GTP, and β-Tubulin

OVCAR-3 cells were plated at a density of $1.5 \times 10^6$ cells in 10-cm plates and grown for 24 h in the presence of 25 or 50 µM FTS. The cells were lysed in 0.5 mL of the Ras-binding domain of Raf-1 (RBD) lysis buffer [Herrmann, C., Martin, G. A. and Wittinghofer, A., J Biol Chem 270:2901-05 (1995)] containing 0.1 mM orthovanadate. Lysates containing 50 µg protein were used to determine total Ras by Western immunoblotting with pan anti-Ras antibody (Ab) and lysates containing 1500 µg protein to determine Ras-GTP by the glutathione S-transferase RBD pull-down assay followed by Western immunoblotting with pan anti-Ras Ab and enhanced chemiluminescence, as previously described [Fridman, M., Maruta, H. and Gonez, J., J Biol Chem 275:30363-71 (2000)]. Mouse anti β-tubulin Ab (AK-15, Sigma) was used at a dilution of 1:500 to confirm equal protein loading.

Results

OVCAR-3 Cells Exhibited Significant Levels of Active Ras and Ras-GTP

Figure 1B:
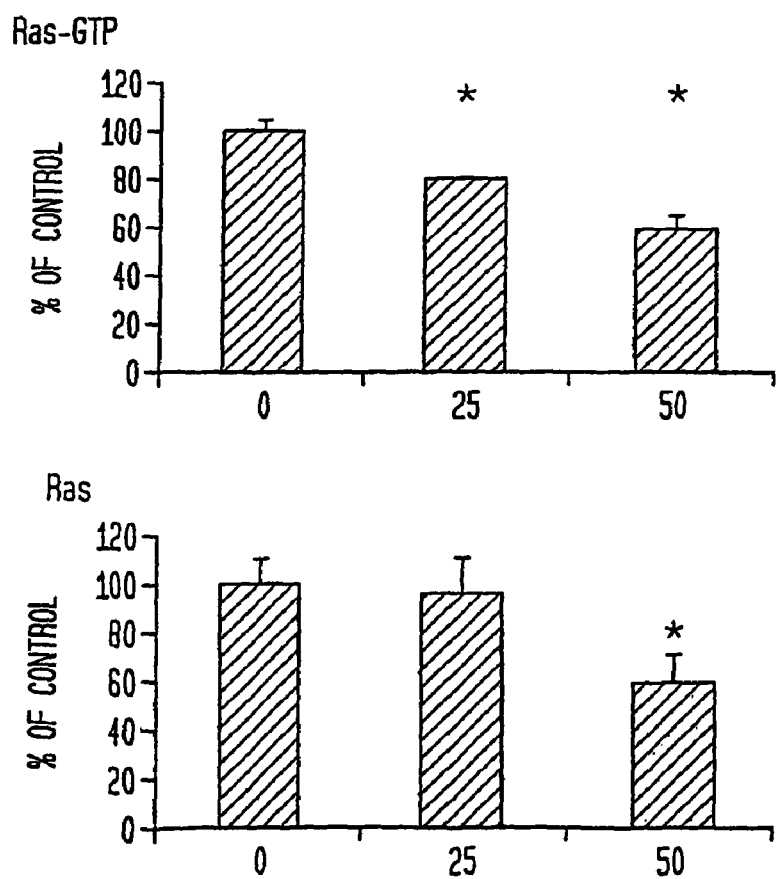
FIG. 1B is a bar graph showing the quantitative analysis of Ras-GTP and Ras in OVCAR-3 cells treated with 0 μM, 25 μM, and 50 μM FTS.

In view of the finding that OVCAR-3 cells expressed significant amounts of Ras and active Ras-GTP (FIGS. 1a and b), Applicants examined whether the Ras antagonist FTS would affect the amounts of Ras and Ras-GTP in these cells in the same way as it affects active Ras in other cell lines [Marom, M., supra.; Elad, G., Paz, A., Haklai, R., Marciano, D., Cox, A., Kloog, Y. Biomed Biochim Acta 8:1452:228-42 (1999); Weisz, B., Giehl, K., Gana-Weisz, M. et al. Oncogene 18:2579-88 (1999)]. The cells were grown for 24 h in serum containing medium with or without 25 or 50 µM FTS. Similar conditions were used in earlier studies with other cell lines [Elad, supra.; Weisz, supra.]. Typical immunoblots (FIG. 1a) yielded by these experiments showed that FTS caused a reduction in the amounts of Ras and Ras-GTP. Quantitative analysis of the immunoblots disclosed that FTS, at concentrations of 25 and 50 µM, caused significant reductions of 5% and 39%, respectively, in Ras and 19% and 41%, respectively, in Ras-GTP (FIG. 1b).

FTS Alone Inhibited Growth in OVCAR-3 Cells

Estimation of the relationship between Ras-GTP and the total amount of Ras showed that the active protein accounts for 4% of total Ras proteins. This indicated that Ras was relatively active in OVCAR-3 cells because in untransformed cells without growth factors stimulation of active Ras accounts for 0.2-0.4% [Niv, H., Gutman, O., Kloog, Y., Henis, Y. I., J Cell Biol 157:865-72 (2002). These results, taken together with the abovementioned estimation, indicated that FTS did not significantly alter the ratio of Ras-GTP to total Ras. We knew from earlier experiments that FTS exerted a direct effect on the membrane bound active Ras protein, dislodging it from the membrane, and had no effect on Ras farnesylation [Haklai, R., Gana-Weisz, G., Elad, G. et al., 37:1306-14 (1998)]. The present results were thus consistent with the known mechanism of action of FTS, whereby a reduction in the amount of active Ras resulted in a shift in the Ras-GTP/Ras-GDP steady state, leading to a depletion of total Ras.

Figure 2:
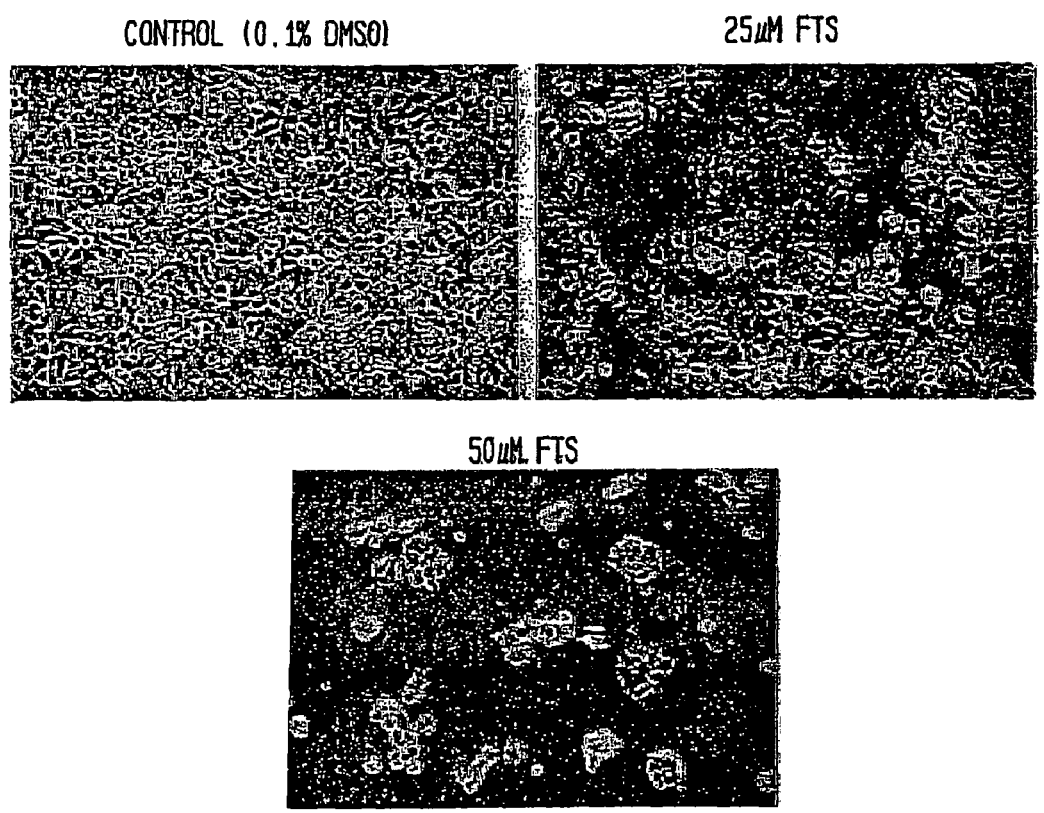
FIG. 2 depicts photomicrograph images (magnification ×100) of OVCAR-3 cells treated with control (0.1% DMSO), 25 μM FTS, or 50 μM FTS.

Anchorage-dependent cell growth was examined in cells that were grown in the presence of FTS. FIG. 2 shows that in the presence of the solvent (0.1% DMSO, control), the cells formed foci typical of malignant transformation. Foci formation and growth were strongly inhibited in cultures maintained for 7 days with 25 or 50 μM FTS (FIG. 2). FTS did not, however, cause cell detachment. In separate experiments, using Hoechst 33258 dye exclusion staining, FTS did not induce cell death under these conditions (data not shown).

FTS Inhibited OVCAR-3 Cell Growth in a Dose-Dependent Manner

Figure 3:
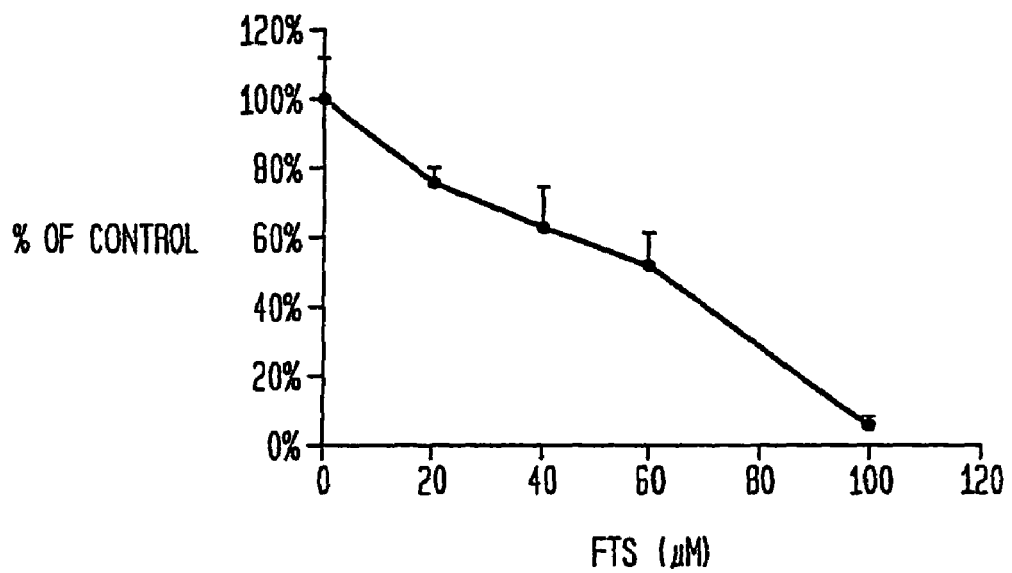
FIG. 3 is a graph showing a dose-response curve of percentage of control versus concentration of FTS (μM) describing inhibition of growth of OVCAR-3 cells by FTS.

FIG. 3 shows that FTS inhibited OVCAR-3 cell growth in a dose-dependent manner. The estimated $IC_{50}$ (concentration of FTS causing 50% inhibition of cell growth) was 54 μM. Comparable results were obtained by direct cell counting (data not shown). The observed $IC_{50}$ value is within the range of FTS concentrations that can be obtained in the blood by a single intraperitoneal administration of FTS in mice, rats, dogs and humans (unpublished data).

FTS Chemosensitized OVCAR-3 Cells to Cisplatin

Figure 4:
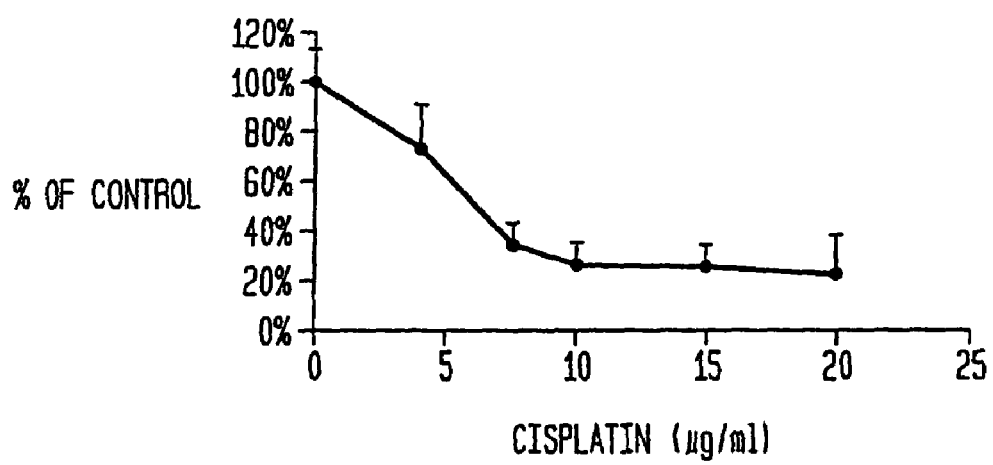
FIG. 4 is a graph showing a dose-response curve of percentage of control versus concentration of cisplatin (μg/ml) describing the cytotoxicity of OVCAR-3 cells by cisplatin.

This cell line was obtained from a patient who was refractory to cisplatin treatment. Cytotoxicity was assayed in the absence of FTS and determined the $IC_{50}$ for cisplatin under the experimental conditions used for the FTS treatments. In agreement with earlier reports [Gibb, R. K., Taylor, D. D., Wan, T., O'Connor, D. M., Doering, D. L., Gercel-Taylor, C. Gynecol Oncol 65:13-22 (1997); Kuroda, H., Mandai, M., Konishi, I. et al. Int J Cancer 76:571-8 (1998)] the $IC_{50}$ of cisplatin was 6.1 μg/mL (FIG. 4). Cisplatin at concentrations of up to 1 μg/mL exhibited no cytotoxic effect and had only a small effect at 2 μg/mL (FIG. 4).

Figure 5:
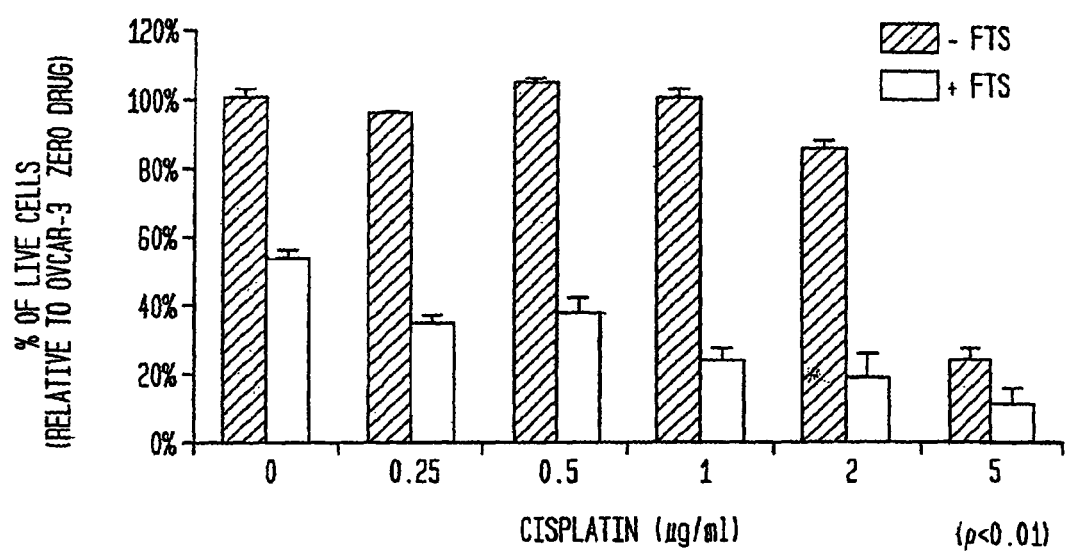
FIG. 5 is a bar graph showing the percentage of live (untreated) OVCAR-3 cells after treatment with 50 μM FTS, either alone or in combination with treatment of increasing concentrations of cisplatin (μg/ml).

The experiment was then repeated while treating the cells with 50 μM FTS, either alone or in combination with increasing concentrations of cisplatin (0.25-5.0 μg/mL). Results indicated that FTS alone caused 45% inhibition of cell growth without cytotoxicity. Combined treatment with 50 μM FTS and 0.25-1.0 μg/mL cisplatin, neither of which was toxic by itself, resulted in death of the OVCAR-3 cells (FIG. 5). As an example, 1 μg/mL cisplatin combined with 50 μM FTS reduced the number of cells by 80% (FIG. 5). Thus, the greater than additive effect of these two drugs was manifested in an additional decrease of 35% in cell number, which was accounted for by death of the cells.

These experiments strongly supported the notion that active Ras is an important target in this human malignancy. In earlier experiments, an attempt was made to inhibit ovarian carcinoma cell growth by the use of farnesyltransferase inhibitors that inhibit farnesylation of H-Ras, which is required for its functions [Rose, W. C., Lee, F. Y., Fairchild, C. R., et al., Cancer Res 61:7507-17 (2001). Farnesyltransferase inhibitors, however, are not Ras inhibitors and do not block the function of the K-Ras, which appears to be the most important Ras isoform in ovarian carcinomas. [Enomoto, T., Weghorst, C. M., Inoue, M., Tanizawa, O., Rice, J. M., Am J Pathol 139:777-85 (1999); Ichikawa, Y., Nishida, M., Suzuki, H. et al., Cancer Res 54:33-5 (1994)].

The publications cited in the specification, patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating ovarian cancer, comprising administering to a human diagnosed with ovarian cancer an effective amount of FTS or an analog thereof represented by the formula:

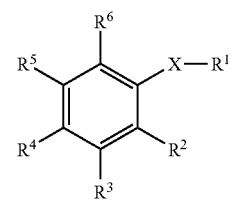

wherein $R^1$ represents farnesyl, geranyl or geranyl-geranyl;

$R^2$ is $COOR^7$, or $CONR^7R^8$, wherein $R^7$ and $R^8$ are each independently hydrogen, alkyl or alkenyl;

$R^3$, $R^4$, $R^5$ and $R^6$ are each independently hydrogen, alkyl, alkenyl, alkoxy, halo, trifluoromethyl, trifluoromethoxy, or alkylmercapto; and X represents S; or a pharmaceutically acceptable salt thereof, and a platinum-based drug.

2. The method of claim 1, wherein the human diagnosed with ovarian cancer is administered farnesylthiosalicylic acid (FTS).

3. The method of claim 1, wherein the analog of FTS is S-geranyl,geranyl-thiosalicylic acid (GGTS).

4. The method of claim 1, wherein the FTS or its analog or a pharmaceutically acceptable salt thereof is administered orally.

5. The method of claim 1, wherein the platinum-based drug is cisplatin.

6. The method of claim 1, wherein the platinum-based drug is carboplatin.

7. The method of claim 1, wherein the platinum-based drug is administered intravenously.

8. A method of inhibiting growth of human ovarian cancer cells, comprising contacting human ovarian cancer cells with an effective amount of FTS or an analog thereof represented by the formula:

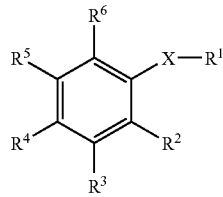

wherein
R¹ represents farnesyl, geranyl or geranyl-geranyl;
R² is COOR⁷, or CONR⁷R⁸, wherein R⁷ and R⁸ are each independently hydrogen, alkyl or alkenyl;
R³, R⁴, R⁵ and R⁶ are each independently hydrogen, alkyl, alkenyl, alkoxy, halo, trifluoromethyl, trifluoromethoxy, or alkylmercapto; and
X represents S; or a pharmaceutically acceptable salt thereof, and an effective amount of a platinum-based drug.

9. A method of chemosensitizing human ovarian cancer cells, comprising contacting human ovarian cancer cells with an effective amount of FTS or an analog thereof represented by the formula:

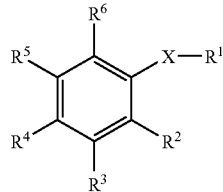

wherein
R¹ represents farnesyl, geranyl or geranyl-geranyl;
R² is COOR⁷, or CONR⁷R⁸, wherein R⁷ and R⁸ are each independently hydrogen, alkyl or alkenyl;
R³, R⁴, R⁵ and R⁶ are each independently hydrogen, alkyl, alkenyl, alkoxy, halo, trifluoromethyl, trifluoromethoxy, or alkylmercapto; and
X represents S; or a pharmaceutically acceptable salt thereof, and then contacting the cells with an effective amount of a platinum-based drug.

10. A kit for treating a human diagnosed with ovarian cancer, comprising:
printed materials including instructions for treating a human diagnosed with ovarian cancer; and an effective amount of FTS or an analog thereof represented by the formula:

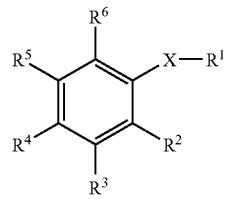

wherein
R¹ represents farnesyl, geranyl or geranyl-geranyl;
R² is COOR⁷, or CONR⁷R⁸, wherein R⁷ and R⁸ are each independently hydrogen, alkyl or alkenyl;
R³, R⁴, R⁵ and R⁶ are each independently hydrogen, alkyl, alkenyl, alkoxy, halo, trifluoromethyl, trifluoromethoxy, or alkylmercapto; and
X represents S; or a pharmaceutically acceptable salt thereof and an effective amount of a platinum-based drug.

* * * * *